(12) United States Patent
Legangneux

(10) Patent No.: US 8,492,441 B2
(45) Date of Patent: Jul. 23, 2013

(54) DOSAGE REGIMEN OF AN S1P RECEPTOR AGONIST

(75) Inventor: Eric Legangneux, Basel (CH)

(73) Assignee: Novartis AG, Basel (CH)

( * ) Notice: Subject to any disclaimer, the term of this patent is extended or adjusted under 35 U.S.C. 154(b) by 344 days.

(21) Appl. No.: 12/655,049

(22) Filed: Dec. 21, 2009

(65) Prior Publication Data

US 2011/0039818 A1     Feb. 17, 2011

Related U.S. Application Data

(60) Provisional application No. 61/139,673, filed on Dec. 22, 2008.

(30) Foreign Application Priority Data

Aug. 4, 2009   (EP) ..................................... 09167209

(51) Int. Cl.
    *A61K 31/15*     (2006.01)

(52) U.S. Cl.
    USPC ........................................................ 514/640

(58) Field of Classification Search
    USPC ........................................................ 514/640
    See application file for complete search history.

(56) References Cited

FOREIGN PATENT DOCUMENTS

| WO | WO 2005/058316 | 6/2006 |
|---|---|---|
| WO | WO 2009/048993 | 4/2009 |

OTHER PUBLICATIONS

Schmoulder R., et al., Oral fingolimod (FTY720), 0.5 or 1.25 mg, for 14 days has no effect on cardiac function: "World Congression Treatment and Research on Multiple Sclerosis", vol. 14, p. S177, (Sep. 2008).

Budde K et al., "First human trial of FTY720, a novel immunomodulator, in stable renal transplant patients", Journal of the American Society of Nephrology, vol. 13, No. 4, pp. 1073-1083, Jan. 2002.

Koyrakh Iev et al., "The heart rate decrease caused by acute FTY720 administrated is mediated by the G protein-gated potassium channel 1", American Journal of Transplantation: Offical Journal of the American Society of Transplantation and the American Society of Transplant Surgeons, vol. 5, No. 3, pp. 529-536, (mar. 2005).

*Primary Examiner* — Paul Zarek
(74) *Attorney, Agent, or Firm* — Karen DeBenedictis

(57) ABSTRACT

S1P receptor modulators or agonists are administered following a dosage regimen whereby during the initial days of treatment the daily dosage is lower than the standard daily dosage.

16 Claims, 2 Drawing Sheets

DOSAGE REGIMEN OF AN S1P RECEPTOR AGONIST

This application claims benefit of U.S. Provisional Application No. 61/139,673, filed Dec. 22, 2008, and EP Application No. 09167209.7 filed Aug. 4, 2009, which in their entirety are herein incorporated by reference.

FIELD OF THE INVENTION

The present invention relates to a dosage regimen for a S1P receptor modulator or agonist. More specifically, the present invention relates to a dosage regimen for the treatment of patients suffering from autoimmune diseases or disorders, such as, for example, multiple sclerosis with a S1P receptor modulator or agonist.

S1P receptor modulators or agonists are compounds which signal as agonists at one or more sphingosine-1 phosphate receptors, for example, S1P1 to S1P8. The binding of an agonist to a S1P receptor may, for example, result in the dissociation of intracellular heterotrimeric G-proteins into Gα-GTP and Gβγ-GTP, and/or the increased phosphorylation of the agonist-occupied receptor, and/or the activation of downstream signaling pathways/kinases.

S1P receptor modulators or agonists are useful therapeutic compounds for the treatment of various conditions in mammals, especially in human beings. For example, the efficacy of S1P receptor modulators or agonists in the prevention of transplant rejection has been demonstrated in rat (skin, heart, liver, small bowel), dog (kidney), and monkey (kidney) models. In addition, due to their immune-modulating potency, S1P receptor modulators or agonists are also useful for the treatment of inflammatory and autoimmune diseases. In particular, the efficacy of the S1P receptor agonist FTY720 in the treatment of multiple sclerosis has been demonstrated in humans (as described in, for example, "FTY720 therapy exerts differential effects on T cell subsets in multiple sclerosis". Mehling M, Brinkmann V, Antel J, Bar-Or A, Goebels N, Vedrine C, Kristofic C, Kuhle J, Lindberg R L, Kappos L. Neurology. 2008 Oct. 14; 71(16):1261-7; and "Oral fingolimod (FTY720) for relapsing multiple sclerosis". Kappos L, Antel J, Comi G, Montalban X, O'Connor P, Polman C H, Haas T, Kom A A, Karlsson G, Radue E W; FTY720 D2201 Study Group. N Engl J. Med. 2006 Sep. 14; 355(11):1124-40).

Multiple sclerosis is the chief cause of neurological disability in young adults and the most common demyelinating disorder of the central nervous system. Currently available therapies, such as interferon-β and glatiramer acetate, have only modest efficacy and therefore demonstrate only marginal effects on the progression of the disease. Furthermore, these biological agents are administered parenterally and are associated with some adverse effects such as, for example, localized reactions at the injection site and pyretic symptoms. Therefore, there is a strong medical need for an effective oral treatment for multiple sclerosis.

S1P receptor modulators or agonists may produce a negative chronotropic effect e.g. at therapeutic doses, i.e. they may reduce the cardiac rhythm, as described e.g. in "FTY720: Placebo-Controlled Study of the Effect on Cardiac Rate and Rhythm in Healthy Subjects", Robert Schmouder, Denise Serra, Yibin Wang, John M. Kovarik, John DiMarco, Thomas L. Hunt and Marie-Claude Bastien. J. Clin. Pharmacol. 2006; 46; 895. Administration of 1.25 mg of FTY720 may induce a decrease in heart rate of approximately 8 beats/min (BPM).

As a consequence of this side effect, the S1P modulator or agonist therapy may have to be initiated under close medical supervision in order to check that the cardiac rhythm is maintained at an acceptable level. This may involve the hospitalization of patients, which makes the treatment more expensive and complicated.

Therefore, there is a need to reduce the negative chronotropic side effect that may be generated by the administration of S1P receptor modulators or agonists, while maintaining the ability to administer an adequate dosage in order to treat or prevent the diseases for which the compound is administered. There is furthermore a need to enhance patient compliance.

BRIEF DISCLOSURE OF THE INVENTION

In a first aspect of the invention, there is provided the use of a S1P receptor modulator or agonist in the manufacture of a medication, whereby said S1P receptor modulator or agonist is given at a dosage lower than the standard daily dosage of said S1P receptor modulator or agonist during the initial period of treatment and then is increased, optionally stepwise, up to the standard daily dosage of said S1P receptor agonist. In accordance with the invention, the medication may be for the treatment of a long term chronic condition. The medication may, for example, be for the treatment of an autoimmune condition such as multiple sclerosis.

In a further aspect of the invention, there is provided the use of a S1P receptor modulator or agonist, that induces a negative chronotropic effect in a patient (e.g. at therapeutic dosage), in the manufacture of a medication, wherein, prior to commencing the administration of the S1P receptor modulator or agonist at its standard daily dosage, said S1P receptor modulator or agonist is administered, during an initial period of treatment, at a daily dosage which is lower than the standard daily dosage.

In a further aspect of the invention, there is provided a method for treating a patient in need thereof (e.g. a patient suffering from a long term condition, an autoimmune condition e.g. multiple sclerosis), such a method comprising administering a S1P receptor modulator or agonist which induces a negative chronotropic effect in heart rate, to the subject, during an initial period of treatment, at a daily dosage which is lower than the standard daily therapeutic dosage and thereafter commencing the administration of said S1P receptor modulator or agonist at the required standard daily therapeutic dosage.

In a further aspect of the invention, there is provided a method of ameliorating or preventing a negative chronotropic side effect associated with a treatment using an S1P modulator or agonist (e.g. compound A or a salt or prodrug thereof) of a subject suffering from an autoimmune disease, comprising administering to the subject in need thereof, said S1P receptor modulator or agonist at a daily dosage which is lower than the standard daily dosage during an initial treatment period and raising the daily dosage stepwise up to the standard daily dosage.

In a further aspect of the invention, there is provided a kit containing daily units of medication of an SW receptor modulator or agonist, e.g. compound A, or a salt or prodrug thereof, of varying daily dosage, whereby said doses are lower than the standard daily dosage.

In a further aspect of the invention, there is provided a kit comprising units of medication of Compound A or a salt or prodrug thereof for administration according to the dosage regimen defined in any of the aspects or embodiments of the invention, whereby one or more low-dose units of a dose strength below the standard daily dose of said compound are provided for the initial period of treatment.

Further aspects and embodiments are provided in the detailed disclosure of the invention.

DETAILED DISCLOSURE OF THE INVENTION

Figure 1:
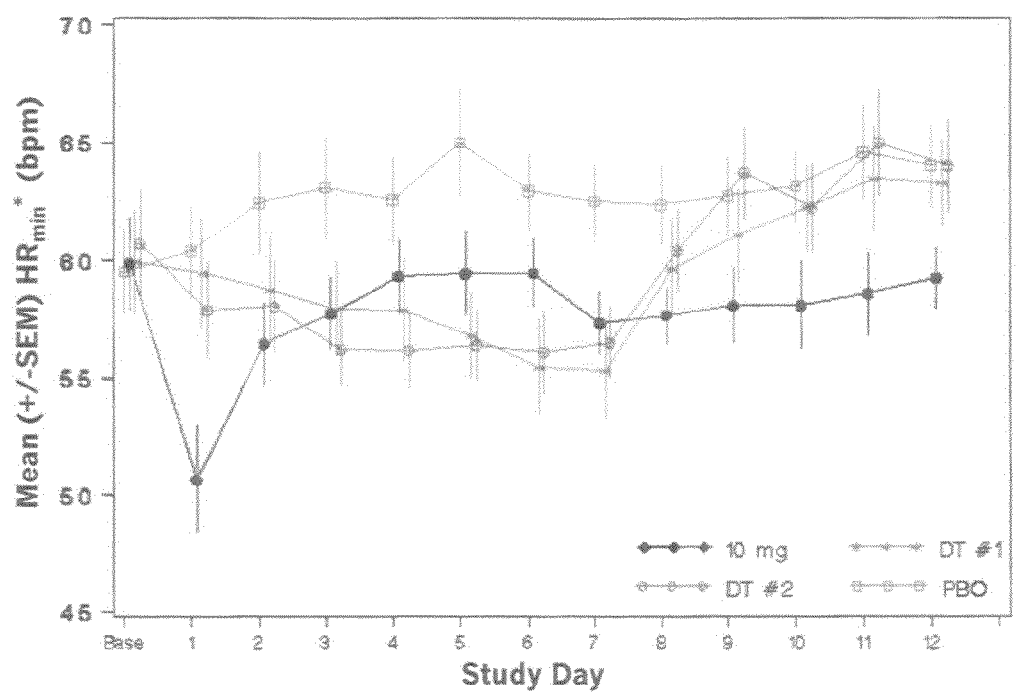
FIG. 1 shows the variation in daily minimum heart rate of patients administered with placebo and with compound A under different titration regimes.

Surprisingly it has been found that by administering the S1P receptor modulator or agonist according to a specific dosage regimen, it is possible to reduce side effects which may be associated with the administration of such compounds. For example, administering a S1P receptor agonist or modulator according to the specific dosage regimen of the present invention may significantly reduce, or even completely eliminate, the negative chronotropic side effect. In particular, it may avoid an abrupt drop in the heart rate.

Administering a S1P receptor agonist or modulator according to the specific dosage regimen of the present invention may also significantly reduce or even completely eliminate the risk that the patient taking the S1P receptor agonist or modulator suffers from heart effects e.g. atrio-ventricular (AV) blocks or heart pauses.

Furthermore the specific dosage regimen of the present invention permits to administer a S1P receptor agonist or modulator to categories of patients for which the risk/benefit ratio may otherwise be less favourable. Such patients could for example include patients suffering from or susceptible to heart problems e.g. heart failure or arrhythmias, patients suffering from or susceptible to high grade atrio-ventricular blocks or sick sinus syndrome, patients with a history of syncopal episodes, or patients undergoing beta blocker or anti-arrhythmic treatment, such as patients under treatment with anti-arrhythmic drugs; or patients that have undergone an interruption or treatment holiday in the maintenance dosage regime e.g. a holiday of greater than 4 days, greater than 6, 8, 10, 12 or 14 days.

The dosage regimen of the present invention is a regimen for the initiation of S1P receptor modulator or agonist therapy, which enables the standard daily therapeutic dosage range of the S1P receptor to be achieved with minimal negative chronotropic effects and/or the AV block effects possibly associated with S1P receptor modulator therapy.

S1P Receptor Modulators or Agonists

Preferred S1P receptor agonists or modulators are, for example, compounds which, in addition to their S1P binding properties, also have accelerating lymphocyte homing properties. For example, the compounds may elicit lymphopenia resulting from a re-distribution of lymphocytes from the circulation to the secondary lymphatic tissue, which is preferably reversible, without evoking a generalized immunosuppression. Suitably, naïve cells are sequestered and CD4/CD8 T-cells and B-cells from the blood are stimulated to migrate into lymph nodes (LN) and Peyer's patches (PP).

Examples of appropriate S1P receptor agonists or modulators of the present invention are, for example compounds as disclosed in WO 04/103306, WO 05/000833, WO 05/103309 or WO 05/113330, e.g. compounds of formula Ia or Ib

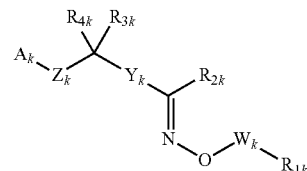

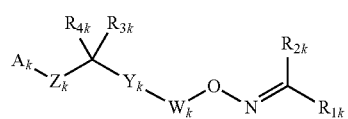

wherein
$A_k$ is —COOR$_{5k}$, —OPO(OR$_{5k}$)$_2$, —PO(OR$_{5k}$)$_2$, —SO$_2$OR$_{5k}$, —POR$_{5k}$OR$_{5k}$ or 1H-tetrazol-5-yl, R$_{5k}$ being H or C$_{1-6}$alkyl; $A_k$ is in particular —COOR$_{5k}$, e.g. —COOH;

$W_k$ is a bond, C$_{1-3}$alkylene or C$_{2-3}$alkenylene; in embodiments, $W_k$ is methylene or ethylene;

$Y_k$ is C$_{6-10}$aryl or C$_{3-9}$heteroaryl, optionally substituted by 1 to 3 radicals selected from halogen, —OH, —NO$_2$, C$_{1-6}$alkyl, C$_{1-6}$alkoxy; halo-substituted C$_{1-6}$alkyl and halo-substituted C$_{1-6}$alkoxy; Y is in particular phenyl or C$_6$heteroaryl, in either case optionally substituted as aforesaid. An exemplary alkyl substituent is ethyl. Halogen is in particular F or Cl.

$Z_k$ is chosen from

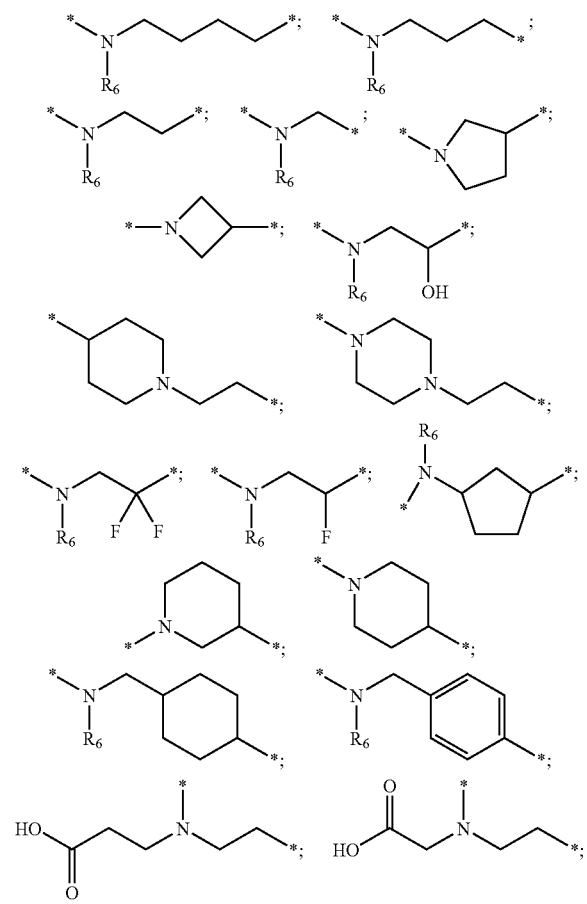

-continued

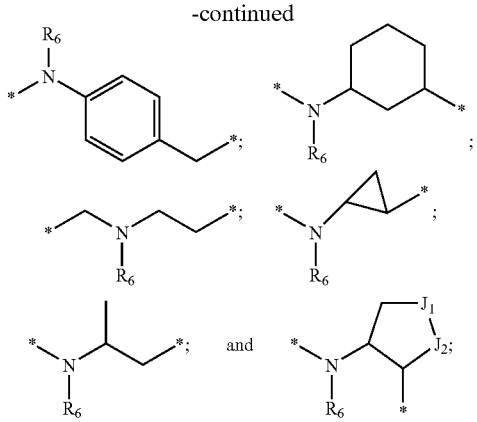

wherein the asterisks of $Z_k$ (e.g. the left and right asterisks) indicate the point of attachment between —C($R_{3k}$)($R_{4k}$)— and A of Formula Ia or Ib, respectively; $R_6$ is chosen from hydrogen and $C_{1-6}$alkyl; and $J_1$ and $J_2$ are independently methylene or a heteroatom chosen from S, O and $NR_{5'}$; wherein $R_{5'}$ is chosen from hydrogen and $C_{1-6}$alkyl; and any alkylene of $Z_k$ can be further substituted by one to three radicals chosen from halo, hydroxy, $C_{1-6}$alkyl; or $R_6$ can be attached to a carbon atom of $Y_k$ to form a 5-7 member ring;

Particularly $Z_k$ is azetidine, pyrrolidine and piperidine, in either case joined to the remainder of the molecule at the 1- and 3-positions e.g. azetidine joined to the remainder of the molecule at the 1- and 3-positions e.g. with the nitrogen at the 1 position joined to the $CR_{3k}R_{4k}$ group; and piperidine 1,4-disubstituted by the respective moieties forming the remainder of the molecule.

$R_{1k}$ is $C_{6-10}$aryl or $C_{3-9}$heteroaryl, optionally substituted by $C_{1-6}$alkyl, $C_{6-10}$aryl, $C_{6-10}$aryl$C_{1-4}$alkyl, $C_{3-9}$heteroaryl, $C_{3-9}$heteroaryl$C_{1-4}$alkyl, $C_{3-8}$cycloalkyl, $C_{3-8}$cycloalkyl$C_{1-4}$alkyl, $C_{3-8}$heterocycloalkyl or $C_{3-8}$heterocycloalkyl$C_{1-4}$alkyl; wherein any aryl, heteroaryl, cycloalkyl or heterocycloalkyl of $R_{1k}$ may be substituted by 1 to 5 groups selected from halogen, $C_{1-6}$alkyl, $C_{1-6}$alkoxy and halo substituted-$C_{1-6}$alkyl or —$C_{1-6}$alkoxy;

$R_{1k}$ is in particular phenyl or $C_6$heteroaryl optionally substituted as aforesaid. $R_{1k}$ in some embodiments has two substituents selected from optionally halo-substituted alkyl having 1, 2, 3, 4, 5 or 6 carbon atoms (e.g. trifluoromethyl), optionally halo-substituted phenyl and optionally halo-substituted $C_{3-8}$cycloalkyl (e.g. cyclohexyl), for example $R_{1k}$ may have one optionally halo-substituted alkyl group and one optionally halo-substituted cyclic moiety selected from phenyl and $C_{3-8}$(e.g.$C_6$)cycloalkyl groups. $R_{1k}$ is in some compounds phenyl or $C_6$heteroaryl, particularly phenyl, 3,4-disubstituted as aforesaid, as in the case of 3-trifluoromethyl-4-cyclohexylphenyl.

$R_{2k}$ is H, $C_{1-6}$alkyl, halo substituted $C_{1-6}$alkyl, $C_{2-6}$alkenyl or $C_{2-6}$alkynyl: $R_{2k}$ is in particular methyl; and each of $R_{3k}$ or $R_{4k}$, independently, is H, halogen, OH, $C_{1-6}$alkyl, $C_{1-6}$alkoxy or halo substituted $C_{1-6}$alkyl or $C_{1-6}$alkoxy. Alkyl, whether or not halo-substituted and/or part of alkoxy, may therefore have 1, 2, 3, 4, 5 or 6 carbon atoms. $R_{3k}$ and $R_{4k}$ may by way of example each independently be H, halogen, methyl or halo-substituted methyl. In particular, $R_{3k}$ and $R_{4k}$ may both be H;

and the N-oxide derivatives thereof or prodrugs thereof, or a pharmacologically acceptable salt, solvate or hydrate thereof.

Specific compounds of formula Ia and Ib useful for the purposes of the invention include:

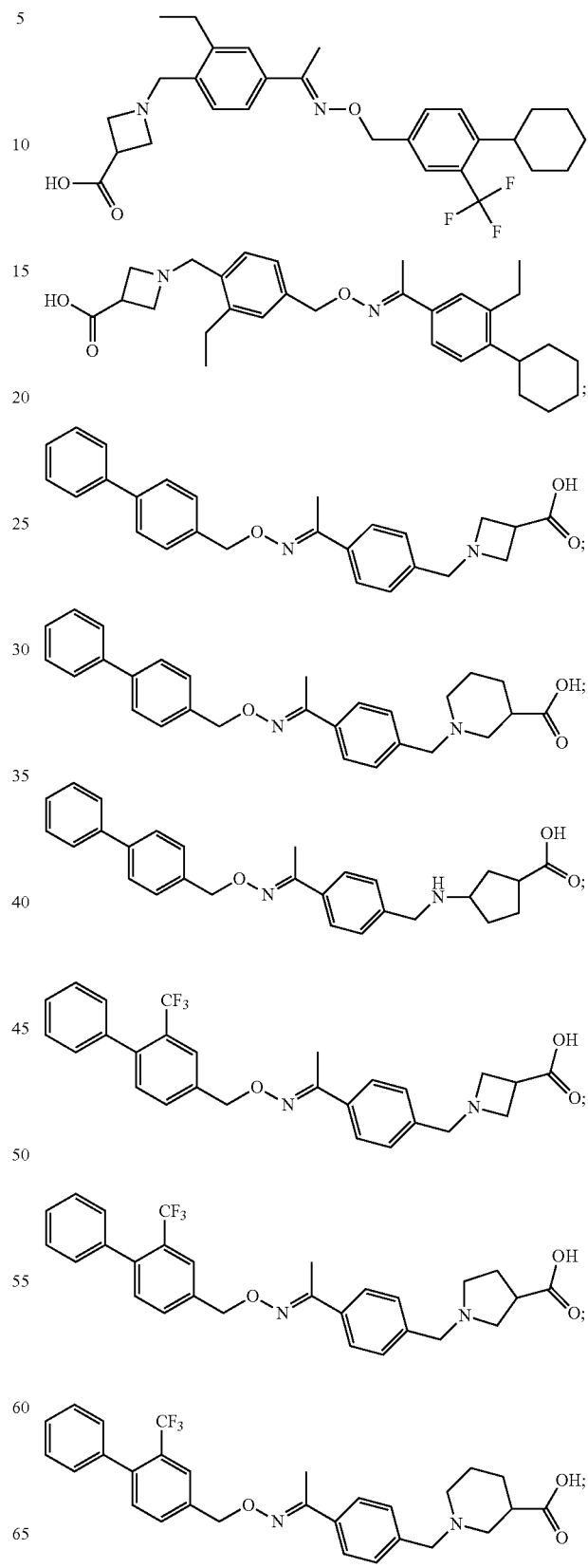

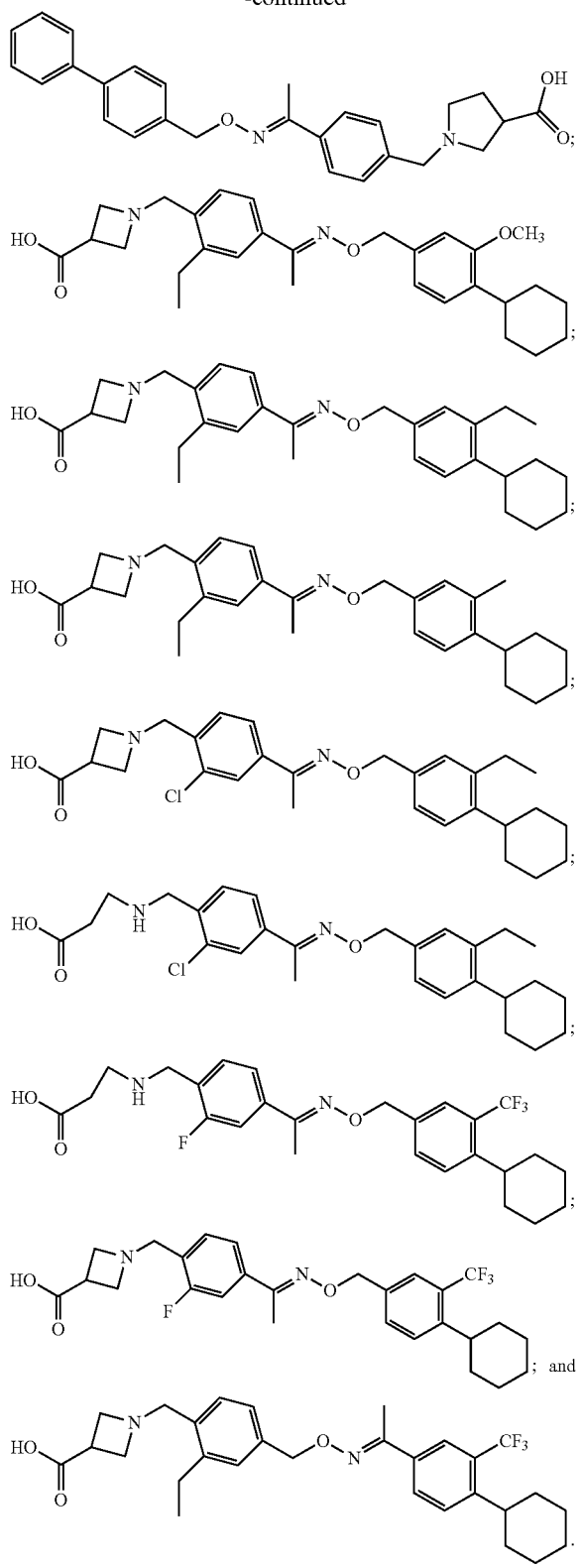

or a pharmaceutically acceptable salt, solvate or prodrug thereof.

Also to be mentioned are other compounds of the Examples set out in Table 1 of WO 2004/103306, the content of which is hereby incorporated by reference.

It will be appreciated that the features specified in each embodiment may be combined with other specified features to provide further embodiments.

When the compounds of formulae Ia or Ib have one or more asymmetric centers in the molecule, the present invention is to be understood as embracing the various optical isomers, as well as racemates, diastereoisomers and mixtures thereof are embraced.

The compounds of formulae Ia or Ib may exist in free or salt form. Examples of pharmaceutically acceptable salts of the compounds of the formulae Ia or Ib include salts with inorganic acids, such as hydrochloride, hydrobromide and sulfate, salts with organic acids, such as acetate, fumarate, hemifumarate, maleate, benzoate, citrate, malate, methanesulfonate and benzenesulfonate salts, or, when appropriate, salts with metals such as sodium, potassium, calcium and aluminium, salts with amines, such as triethylamine and salts with dibasic amino acids, such as lysine. The compounds and salts of the combination of the present invention encompass hydrate and solvate forms.

In the above definitions:

acyl may be a residue $R_y$—CO— wherein $R_y$ is $C_{1-6}$alkyl, $C_{3-6}$cycloalkyl, phenyl or phenyl-$C_{1-4}$alkyl unless otherwise stated, alkyl, alkoxy, alkenyl or alkynyl may be straight or branched;

aryl may be phenyl or naphthyl, preferably phenyl;

"heterocyclic group" represents a 5- to 7 membered heterocyclic group having 1 to 3 heteroatoms selected from S, O and N. Examples of such heterocyclic groups include the heteroaryl groups indicated above, and heterocyclic compounds corresponding to partially or completely hydrogenated heteroaryl groups, e.g. furyl, thienyl, pyrrolyl, azepinyl, pyrazolyl, imidazolyl, oxazolyl, isoxazolyl, thiazolyl, isothiazolyl, 1,2,3-oxadiazolyl, triazolyl, tetrazolyl, thiadiazolyl, pyranyl, pyridyl, pyridazinyl, pyrimidinyl, pyrazinyl, tetrahydropyranyl, morpholinyl, thiomorpholinyl, pyrrolidinyl, pyrrolyl, imidazolidinyl, pyrazolidinyl, piperidinyl, piperazinyl, oxazolidinyl, isoxazolidinyl, thiazolidinyl or pyrazolidinyl. Preferred heterocyclic groups are 5- or 6-membered heteroaryl groups and the most preferred heteocyclic group is a morpholinyl, thiomorpholinyl or piperidinyl group.

A preferred compound of formula Ia is e.g. 1-{4-[1-(4-cyclohexyl-3-trifluoromethyl-benzyloxyimino)-ethyl]-2-ethyl-benzyl}-azetidine-3-carboxylic acid (Compound A), or a salt (e.g. a hemifumarate salt) or prodrug thereof.

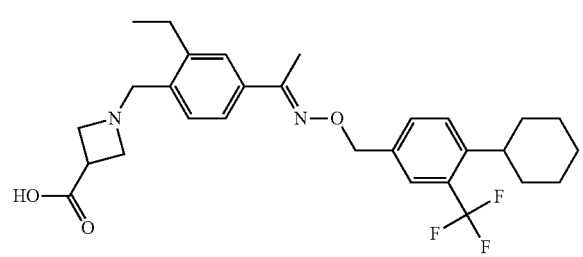 [SMILES: CCc1cc(/C(C)=N/OCc2ccc(C3CCCCC3)c(C(F)(F)F)c2)ccc1CN1CC(C(=O)O)C1]

Prodrugs therefore include drugs having a functional group which has been transformed into a reversible derivative thereof. Typically, such prodrugs are transformed to the active drug by hydrolysis. As examples may be mentioned the following:

| Functional Group | Reversible derivative |
| --- | --- |
| Carboxylic acid | Esters, including e.g. alkyl and acyloxyalkyl esters; amides |
| Alcohol | Esters, including e.g. sulfates and phosphates as well as carboxylic acid (e.g. alkanoic acid) esters |
| Amine | Amides, carbamates, imines, enamines, |
| Carbonyl (aldehyde, ketone) | Imines, oximes, acetals/ketals, enol esters, oxazolidines and thiazoxolidines |

Prodrugs also include compounds convertible to the active drug by an oxidative or reductive reaction. As examples may be mentioned:

Oxidative activation
N— and O— dealkylation
Oxidative deamination
N-oxidation
Epoxidation
Reductive activation
Azo reduction
Sulfoxide reduction
Disulfide reduction
Bioreductive alkylation
Nitro reduction.

Also to be mentioned as metabolic activations of prodrugs are nucleotide activation, phosphorylation activation and decarboxylation activation. For additional information, see "The Organic Chemistry of Drug Design and Drug Action", R B Silverman (particularly Chapter 8, pages 497 to 546), incorporated herein by reference.

In a further embodiment of the invention, a S1P receptor agonist or modulator for use in the dosage regimen of the invention may also be selective for the $S1P_1$ receptor. For example, a compound which possesses selectivity for the $S1P_1$ receptor over the $S1P_3$ receptor of at least 20 fold, e.g. 100, 500, 1000 or 2000 fold, as measured by the ratio of $EC_{50}$ for the $S1P_1$, receptor to the $EC_{50}$ for the $S1P_3$ receptor as measured by a $^{35}S$-GTPγS binding assay, and wherein said compound has an $EC_{50}$ for binding to the S1P1 receptor of 100 nM or less as evaluated by the $^{35}S$-GTPγS binding assay.

The $^{35}S$-GTPγS binding assay is described in WO03/097028 and DS. Im et al., Mol. Pharmacol. 2000; 57:753. Briefly, ligand-mediated GTPγS binding to G-proteins is measured in GTP binding buffer (in mM: 50 HEPES, 100 NaCl, 10 $MgCl_2$, pH 7.5) using 25 µg of a membrane preparation from transiently transfected HEK293 cells. Ligand is added to membranes in the presence of 10 µM GDP and 0.1 nM [$^{35}S$]GTPγS (1200 Ci/mmol) and incubated at 30° C. for 30 min. Bound GTPγS is separated from unbound using the Brandel harvester (Gaithersburg, Md.) and counted with a liquid scintillation counter.

Dosage Regimens

As previously stated, the present invention provides a novel dosage regimen which is adapted to minimize the negative chronotropic effects and/or the heart effects possibly associated with S1P receptor modulator or agonist therapy.

Heart effects include AV blocks, which include first degree AV blocks (e.g. PR intervals greater then 0.2 seconds) and second degree AV blocks e.g. first degree AV blocks. Heart effects include heart pauses e.g. heart pauses greater than 2 seconds.

According to the invention, there is provided the use of a S1P receptor modulator or agonist in the manufacture of a medication, whereby said medication is administered in such a way that during the initial period of treatment the dosage is lower than the standard daily dosage and the dosage is increased, optionally stepwise, or only once, until the standard daily dosage dose is reached. Thereafter the treatment is preferably continued with the standard daily dosage of said S1P receptor modulator or agonist.

Preferably during the initial period of treatment, the medication is administered in a dosage regimen such that daily decrease in heart rate (e.g. average or minimum daily heart rate) is acceptable or clinically not significant, or that the sinus rhythm of the patient is normal. For example, the daily decrease in heart rate (e.g. average or minimum daily heart rate) may be less than about 4 bpm, e.g. less than about 3 bpm or less than about 2 bpm.

The term "normal sinus rhythm" refers to the sinus rhythm of the patient when not undergoing treatment. The evaluation of normal sinus rhythm is within the ability of a physician. A normal sinus rhythm will generally give rise to a heart rate in the range from 60-100 bpm.

According to the invention, the "initial period of treatment" refers to the period during which the S1P receptor modulator or agonist is administered at a dosage lower than the standard daily dosage. Preferably the "initial period of treatment" starts with the first administration of the S1P receptor modulator or agonist.

As herein above defined, standard daily dosage (also called standard daily dose) refers to the daily maintenance dose of the drug which is given to the patients for treating or preventing the disease to be treated or prevented. Preferably, the standard daily dosage corresponds to the therapeutic dosage.

The therapeutically effective dosage (also called therapeutic dose) refers to the dosage of the S1P receptor modulator or agonist which is necessary to effectively treat the intended disease or condition (i.e. so that the subject shows reduced signs or symptoms of the disease to be treated or prevented, or preferably no signs and symptoms of the disease).

The initial period of treatment may be up to 10 days, e.g. 8 to 10 days, for example 9 days or 8 days. Alternatively, the initial period of treatment may be in the range from 5 to 7 days, e.g. six days or seven days. Alternatively, the initial period of treatment may be shorter e.g. in the range from 2 to 4 days, such as 3 or 4 days.

During the initial period of treatment e.g. as the first dose administered, the S1P receptor modulator or agonist may be administered at a dosage up to 80-fold less than the standard daily dosage e.g. up to 40-fold less than the standard daily dose, e.g. the therapeutic dose, e.g. up to 30-fold less, e.g. up to 20-fold less, e.g. up to 10-fold less e.g. up to 5-fold less or up to 3-fold less.

Preferably, the dosage of the S1P receptor modulator or agonist during the initial period of treatment is increased stepwise in a defined incremental ratio up to the standard daily dosage of the S1P receptor modulator or agonist. Preferably, the dosage of said S1P receptor modulator or agonist during the initial 10 days, e.g. 1 to 9 days, of treatment is increased incrementally from 1.5- to 3.5-fold, for example from 2 to 3-fold, for example 2-fold.

In an embodiment, the daily dosage is governed by a Fibonacci series i.e. the dosage given on a specific day is the sum of the dosages on the previous two days. In an aspect of this embodiment, some variation in this scheme is permitted. For example, the dosage on a given day may be the sum of the dosages on the two previous days ±40%, for example ±30%, for example ±20% or ±10%.

During the initial period, the dose may, on any given day, be about 40-fold less, or about 20-fold less, or about 10-fold less, or about 5-fold less, about 2-fold less, or 1.5-fold less than the standard daily dosage, e.g. than the therapeutic dose.

The same dose may be given during the first 1, 2, 3, 4, 5, 6, 7 or 8 days of treatment before the dosage is increased. Preferably the same dose is given during the first 2 to 4 days of treatment e.g. the first two days.

One or more dosage increases, e.g. up to 10 dosage increases, e.g. up to 8 dosage increases, e.g. up to 6 dosage increases, e.g. up to 5 dosage increases, up to 4 dosage increases or up to 3 dosage increases may be performed until the standard daily dosage is given. For example 1 to 10, e.g. 1 to 8, e.g. 2 to 8, e.g. 3 to 6 dosage increases may be given e.g. 2 or 3 dosage increases During the initial phase of treatment, i.e. before the standard daily dosage is given, a same dosage may be given during 1 to 7 days, e.g. 2 to 5 days, before the dosage is further increased, e.g. up to the standard daily dosage.

For example, the first dosage increase may occur on day 2 to day 5, e.g. day 2 to day 4, e.g. day 2, day 3, day 4 or day 5, after the first administration. The second dosage increase, if any, may occur on day 4 to 10, e.g. day 4 to 6, e.g. day 5, after the first administration. The third dosage increase, if any, may occur on day 6 to 10, e.g. day 6 or 7, after first administration.

In one embodiment of the invention, only one dosage increase occurs before the standard daily dosage, e.g. the therapeutic dosage, is given.

In a preferred embodiment, there is provided the use of a S1P receptor modulator or agonist in the manufacture of a medication e.g. for the treatment of a chronic long term disease e.g. an autoimmune condition e.g. multiple sclerosis, whereby said medication is administered in such a way that during the first 10 days of treatment, e.g. 7 to 10 days, for example 10 days, 9 days, 8 days, 7 days, 6 days or 5 days, the dosage of said S1P receptor modulator or agonist is given at an initial dosage of up to 80 fold less, e.g. up to 40-fold less, e.g. up to 30-fold less, e.g. up to 20-fold less e.g. up to 10, 5 or 3-fold less, than the standard daily dose, e.g. the therapeutic dose. Optionally the dose is then raised stepwise up to the standard daily dose, e.g. the therapeutic dose.

Figure 2:
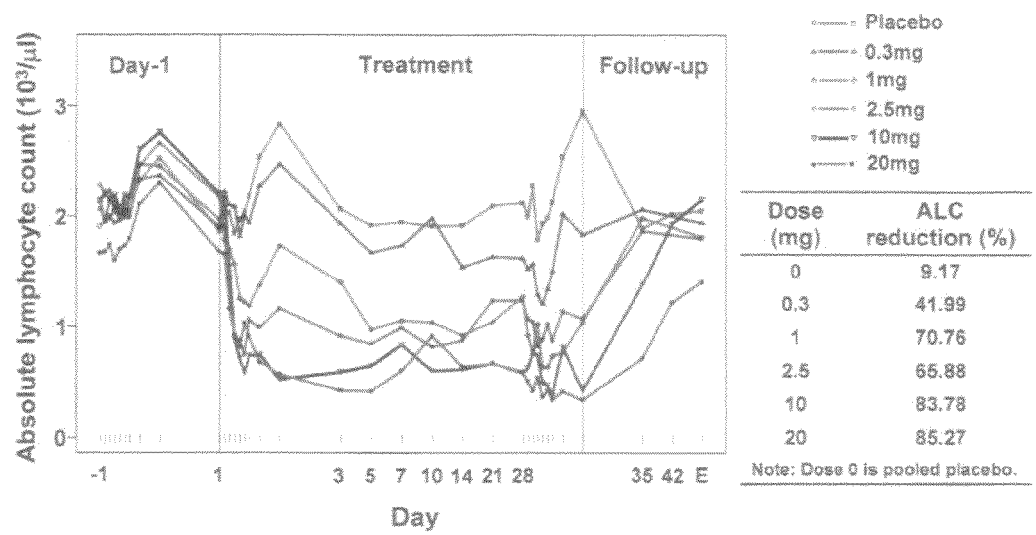
FIG. 2 shows the mean change in absolute lymphocyte count after multiple daily doses of compound A in healthy subjects.

Preferred medications comprise medication for patients suffering from chronic longterm diseases, such as autoimmune diseases, e.g. multiple sclerosis, Polymyositis, lupus nephritis, rheumatoid arthritis, inflammatory bowel diseases or psoriasis. In an embodiment of the invention, medications are medications for patients suffering from multiple sclerosis, for example relapse remitting multiple sclerosis (RRMS) or primary progressive multiple sclerosis (PPMS), e.g. for patients suffering from RRMS. As seen in FIG. 2, administration of compound A reduces the absolute lymphocyte count in the blood of healthy subjects.

The dosage regimen of the present invention is particularly useful for treating patients at risk of cardiac side effects, for example patients at risk of heart failure, arrythmias, patients with high grade atrio-ventricular blocks or sick sinus syndrome, patients with a history of syncopal episodes, or patients requiring or under beta blockers, or patients requiring or under anti-arrhythmic treatment, such as patients under treatment with Class Ia (e.g. quinidine, procainamide) or Class III anti-arrhythmic drugs (e.g., amiodarone, sotalol).

The standard daily dosage is selected to give the optimum balance of efficacy vs safety. According to the invention, the standard daily dosage e.g. the therapeutic dosage of the S1P receptor modulator, e.g. compound A is preferably in the range from about 25 to about 0.1 mg.

In an embodiment, the standard daily dosage e.g. the therapeutic dosage may be in the range from about 25 to about 15 mg, e.g. about 22 to about 18 mg. Alternatively, the standard daily dosage e.g. the therapeutic dosage may be in the range from about 15 to about 11 mg, e.g. about 14 to about 12 mg. In another embodiment, the standard daily dosage e.g. the therapeutic dosage may be in the range from about 11 to about 9 mg, e.g. about 10 mg. Alternatively, the standard daily dosage e.g. the therapeutic dosage may be in the range from about 9 to about 5 mg, e.g. about 8 to about 6 mg. The standard daily dosage e.g. the therapeutic dosage may be in the range from about 5 to about 3 mg, or about 3 to about 1 mg. Alternatively, the therapeutic dose may be in the range from about 1 to about 0.6 mg, about 0.6 to about 0.4 mg, about 0.4. to about 0.2 mg, or about 0.2 to about 0.1 mg.

For compound A, an example of standard daily dosage may be a daily dosage comprised between 8 and 10 mg, e.g. may be 10 or 8 mg. Alternatively, the compound A standard daily dosage may be as specified in the preceeding paragraph.

According to a preferred embodiment of the invention, the highest initial dosage is between 0.25 mg and 0.5 mg, preferably 0.25 mg. This is particularly the case for Compound A.

A particularly preferred dosage range of the S1P receptor modulator or agonist is e.g. 0.1-10 mg, e.g. 0.2-10 mg, e.g. 0.25-10 mg during the initial period of treatment.

For example during the first days of treatment, e.g. up to the first 10-12 days, the regimen may be of 0.25 mg/0.5/10 mg, respectively; or 0.25 mg/0.5/2/4/10 mg, respectively; or 0.25 mg/0.5/1/2/4/8/10 mg. Alternatively, the regimen may be 0.25 mg/0.25 mg/0.5 mg/0.75 mg/1.25 mg/2 mg/3 mg/5 mg/8 mg/10 mg/10 mg/10 mg. Suitably, these dosage regimens are administered according to a Fibonacci series i.e. the dosage given on a specific day is the sum of the dosages on the previous two days, optionally with a variation on any day of ±40%, e.g. ±30%, ±20%, or ±10% of the sum of the dosages of the previous two days. These regimens are particularly adapted for compound A.

Thereafter the treatment is continued with the standard daily dosage.

In a series of further specific or alternative embodiments, the present invention also provides:

1.1 The use of a S1P receptor modulator or agonist which induces a negative chronotropic effect in heart rate, e.g. compound A or a salt or prodrug thereof, in the manufacture of a medication, whereby said medication is administered in such a way to a subject that the daily decrease in heart rate (e.g. the average or minimum daily heart rate) is of about 2 beats/min or less.

1.2 The use of a S1P receptor modulator or agonist, e.g. compound A, or a salt or prodrug thereof, in the manufacture of a medication, whereby said medication is administered in such a way to a subject that at the day the therapeutic dosage of said S1P receptor modulator or agonist is administered the decrease in heart rate (e.g. the average or minimum daily heart rate) is of 2 beats/min or less.

1.3 The use of a S1P receptor modulator or agonist, e.g. compound A or a salt or prodrug thereof, in the manufacture of a medication, whereby said medication is administered at a lower dosage than standard dosage, e.g. dosage of up to 80 fold less e.g. up to 40-fold less, e.g. up to 30-fold less, than the standard daily dosage, during the initial period, e.g. during the first 10 days of treatment. Optionally the dosage is then increased stepwise up to the standard daily dosage, e.g. the therapeutic dosage, of said S1P receptor agonist.

1.4 A method for providing an S1P receptor agonist treatment, whereby said S1P receptor agonist is administered in such a way that during the initial period of treatment, the S1P receptor agonist treatment is administered at a daily dosage lower than the standard daily dosage and the daily dosage is raised up to the standard daily dosage and thereafter the treatment is continued with the standard daily dosage.

1.5 A S1P receptor modulator or agonist for use in the manufacture of a medication, whereby said S1P receptor modulator or agonist is given at a dosage lower than the standard daily dosage of said S1P receptor modulator or agonist during the initial period of treatment and then is increased, optionally stepwise, up to the standard daily dosage of said S1P receptor agonist.

1.6 Use of a S1P receptor modulator or agonist, which at therapeutic dosage induces a negative chronotropic effect in a patient, in the manufacture of a medication, wherein, prior to commencing the administration of the S1P receptor modulator or agonist at its standard daily dosage, said S1P receptor modulator or agonist is administered, during an initial period of treatment, at a daily dosage which is lower than the standard daily dosage.

1.7 Use of a S1P receptor modulator or agonist e.g. a compound of formula Ia or Ib as defined above which at therapeutic dosage induces a negative chronotropic effect in heart rate in the manufacture of a medication e.g. for the treatment of an autoimmune condition e.g. multiple sclerosis, whereby said medication is administered in such a way to a subject that at the day the therapeutic dosage of said S1P receptor modulator or agonist is administered the decrease in heart rate is of 2 bit/min or less.

During the initial period of treatment, e.g. the initial 10 days, e.g. 9 days, 8, 7 or 6 days of treatment, the daily dosage of the S1P receptor modulator or agonist is lower than the standard dosage, and is raised stepwise up to 6 times, e.g. two or three times, up to the standard daily dosage of said S1P receptor modulator or agonist and thereafter the treatment is continued with the standard daily dosage of said S1P receptor modulator or agonist.

1.8 The use of a S1P receptor modulator or agonist, e.g. compound A or a salt or prodrug thereof, in the manufacture of a medication, whereby said medication is administered in such a way that during the initial period of treatment, e.g. the initial 10 or 8 days of treatment, or 7 to 6 days of treatment, the dosage of said S1P receptor modulator or agonist is between 40 fold and 1.25 fold less than the standard daily dosage; for example 40 fold, 20 fold, 10 fold, 5 fold, and 2-3 fold less than the standard daily dosage, respectively, and thereafter the treatment is continued with the standard daily dosage of said S1P receptor modulator or agonist.

1.9 The use of a S1P receptor modulator or agonist, e.g. compound A, or a salt or prodrug thereof, in the manufacture of a medication, whereby said medication is administered in such a way that during the initial 2 to 4 days of treatment the dosage of said S1P receptor modulator or agonist is not more than 1/80, 1/40, 1/30, 1/20 or 1/10, of the standard daily dose of said S1P receptor modulator or agonist.

1.10 The use of an S1P receptor modulator or agonist, e.g. compound A, or a salt or prodrug thereof, in the manufacture of a medication, whereby said medication is administered in such a way that during the initial 10 days, e.g. 9 days, 8, 7 or 6 days, e.g. 6 days, of treatment the dosage of said S1P receptor modulator or agonist is lower than the standard daily dosage of said S1P receptor modulator or agonist and then the dosage is raised so that the standard daily dosage is administered after several dose increases, up to 10, e.g. up to 6, e.g. two or three dose increases, and thereafter the treatment is continued with the standard daily dosage of said S1P receptor agonist.

1.11 Use of a S1P receptor modulator or agonist e.g. a compound of formula Ia or Ib as defined herein which at therapeutic dosage induces a negative chronotropic effect in a patient in the manufacture of a medication e.g. for the treatment of an autoimmune condition, e.g. multiple sclerosis, wherein, prior to commencing the administration of the S1P receptor modulator or agonist at its standard daily dosage, said S1P receptor modulator or agonist is administered at a daily dosage which is lower than the standard daily dosage during an initial period of treatment.

1.12 Use of Compound A, or a pharmaceutically acceptable salt or prodrug thereof, in the manufacture of a medicament for use in the treatment of autoimmune diseases, wherein, prior to commencing the administration of Compound A, or a pharmaceutically acceptable salt or prodrug thereof, at the standard daily dosage, said compound is administered at a daily dosage which is lower than the standard daily dosage during an initial period of treatment (e.g. up to 10 days).

1.13 Use as defined in paragraphs 1.1 to 1.12, wherein the initial period of treatment is of up to 10 days, e.g. up to 8 days, e.g. a week or 6 days; or 3-5 days e.g. 3 or 4 days.

1.14 The use of compound A in the manufacture of a medication, whereby said medication is administered, after an initial regimen as hereinabove defined, at a daily dosage of about 10 mg, or about 8 mg.

1.15 The use as defined in paragraphs 1.1 to 1.14 wherein the medication is given to patient who is suffering from heart problems e.g. is at risk of heart failure.

1.16 Use as defined in paragraphs 1.1 to 1.15, for treating an autoimmune disease, e.g. multiple sclerosis.

1.17 The use of a S1P receptor modulator or agonist, e.g. compound A, or a salt or prodrug thereof, in the manufacture of a medication, whereby said medication is administered in such a way to a subject that the possible risk of AV block is limited or reduced to a level clinically not significant. Preferably the use is then as defined under 1.1 to 1.16.

1.18 The use of a S1P receptor modulator or agonist, e.g. compound A or a salt or prodrug thereof, in the manufacture of a medication, whereby said medication is administered in such a way to a subject that the sinus rhythm of the patient is normal during the administration of the medication to the patient. Preferably the use is then as defined under 1.1 to 1.16.

1.19 The use as defined under 1.1 to 1.16 wherein the medication is given to a patient who is at risk of AV block.

1.20 The use as defined under 1.1 to 1.16 wherein the medication is given to a patient who experiences symptoms including dizziness, fatigue, palpitations.

1.21 The use as defined under 1.1 to 1.16 wherein the medication is given to a patient with high grade atrio-ventricular blocks or sick sinus syndrome.

1.22 The use as defined under 1.1 to 1.16 wherein the medication is given to a patient with arrhythmias, e.g. requiring or under treatment with Class Ia (e.g. quinidine, procainamide) or Class III anti-arrhythmic drugs (e.g. amiodarone, sotalol).

1.23 The use as defined under 1.1 to 1.16 wherein the medication is given to a patient requiring or under beta-blocker therapy.

1.24 The use as defined under 1.1 to 1.23 wherein the medication is given to a patient, e.g. a patient suffering from multiple sclerosis, wherein the administration of said S1P receptor modulator or agonist, e.g. compound A or a salt or prodrug thereof, has been discontinued for more than 4 days, e.g. more than 6, 8 or 10 days, e.g. more than 12 days, e.g. more than 14 days.

The invention further provides:

2.1 A treatment method with a S1P receptor modulator or agonist, e.g. compound A, or a salt or prodrug thereof, the improvement being that said S1P receptor modulator or agonist is administered in such a way that during the initial period of treatment, e.g. the initial 10 days, e.g. 9 days, 8, 7 or 6 days, of treatment, the dosage is lower than the standard dosage, e.g. of up to 80-fold less, e.g. up to 40-fold less, e.g. 30-fold less, than the standard daily dosage, and is increased, optionally stepwise, up to the standard daily dosage. Thereafter the treatment is continued with the standard effective daily dosage.

2.2 A method for treating a patient in need thereof such a method comprising administering a S1P receptor modulator or agonist which induces a negative chronotropic effect in heart rate, e.g. compound A or a salt or prodrug thereof, in such a way that at the day the therapeutic dosage is administered the decrease in heart rate (e.g. the average or minimum daily heart rate) is clinically not significant, preferably is limited to 2 beats/min or less.

2.3 A method as defined under 2.1 and 2.2 comprising administering to the subject sub-therapeutic doses of the S1P receptor agonist during the initial period of treatment.

2.4 A method for treating a chronic longterm disease as herein above defined, an autoimmune disease e.g. multiple sclerosis in a subject in need thereof, comprising administering to the subject, a loading regimen of a S1P receptor modulator or agonist, e.g. compound A, or a salt or prodrug thereof, at a daily dosage which is lower than the standard daily dosage.

2.5 A method for treating an autoimmune disease in a subject in need thereof, comprising administering to the subject, a S1P receptor modulator or agonist, e.g. compound A, or a salt or prodrug thereof, at a daily dosage which is lower than the standard daily dosage during the initial period of treatment, e.g. the first 10 days, 9 days, 8, 7, or 6 days and raising the daily dosage stepwise up to the standard daily dosage.

2.6 A method for treating an autoimmune disease in a subject in need thereof, comprising administering to the subject, an initial regimen up to 80-fold less, e.g. 40-fold less, e.g. 30-fold less than the standard daily dosage, and thereafter the daily dosage of a S1P receptor modulator or agonist, e.g. compound A, or a salt or prodrug thereof.

2.7 A method of ameliorating or preventing a negative chronotrophic side effect associated with a treatment using an S1P modulator or agonist, e.g. compound A, or a salt or prodrug thereof, of a subject suffering from an autoimmune disease, comprising administering to the subject in need thereof, said S1P receptor modulator or agonist at a daily dosage which is lower than the standard daily dosage during an initial treatment period and raising the daily dosage stepwise up to the standard daily dosage.

2.8 A method of treating an autoimmune disease in a patient in need of such treatment, the method comprising administering Compound A, or a pharmaceutically acceptable salt or prodrug thereof, at a daily dosage which is lower than the standard daily therapeutic dosage during an initial period of treatment and thereafter commencing the administration of said compound at the required standard daily therapeutic dosage.

2.9 A method of ameliorating or preventing a negative chronotrophic side effect associated with the treatment of an autoimmune disease with Compound A, or a pharmaceutically acceptable salt or prodrug thereof, the method comprising administering Compound A at a daily dosage which is lower than the standard daily dosage during an initial treatment period and then raising the daily dosage, optionally stepwise, up to the standard daily dosage.

2.10 A method as defined in paragraphs 2.1 to 2.9 whereby the initial period of treatment is of up to 10 days, e.g. up to 8 days, e.g. a week or 6 days.

2.11 A method as defined in paragraphs 2.1 to 2.9 wherein the initial treatment period is 6-14 days e.g. 7-10 days or e.g. 6 days, 7 days or less, as herein above described.

2.12 A method as defined in paragraphs 2.1 or 2.9 for treating an autoimmune disease, e.g. multiple sclerosis.

In another aspect there is provided:

3.1 A S1P receptor modulator or agonist as defined herein for use in the treatment of an autoimmune disease wherein the S1P receptor modulator or agonist is administered according to a dosage regimen as defined herein.

3.2 Compound A, or a salt or prodrug thereof, for use in the treatment of an autoimmune disease (e.g. multiple sclerosis) wherein said compound is administered according to a dosage regimen as defined herein.

In another aspect there is provided:

4.1 A kit containing daily units of medication of an S1P receptor modulator or agonist, e.g. compound A, or a salt or prodrug thereof, of varying daily dosage, whereby said doses are lower than the standard daily dosage. For example, the daily units of said S1P receptor modulator or agonist may be about ¼₀, ¹⁄₁₀ and ½ of the standard dose of the S1P receptor modulator or agonist, respectively; or about ¹⁄₃₀, ¹⁄₁₅ and ⅛; or about ¹⁄₁₀, ⅕ and ½.₅ of the standard daily dose, or about ¹⁄₁₀ or ¼ of the standard dose. In an aspect, the kit comprises 0.5 mg, 2 mg and 10 mg dosages. The kit may further comprise units for the standard daily dosage of the S1P receptor modulator or agonist, e.g. compound A, or a salt or prodrug thereof. The kit may also contain instructions for use.

4.2 A kit comprising units of medication of a Compound A or a salt or prodrug thereof for administration according to the dosage regimen defined herein, whereby one or more low-dose units of a dose strength below the standard daily dose of said compound are provided for the initial period of treatment. In an embodiment, the kit may comprise just one low dose unit of medication at a dosage strength corresponding to an initial dosage of the S1P receptor modulator or agonist. A patient may then take one unit of the low dose medication for a specified number of days and then, optionally, two or more units per day on subsequent days until therapy is commenced with a unit of medication that comprises the standard daily dose of the S1P receptor agonist. In an alternative embodiment, the kit may comprise a number of low-dose units of medication with a range of dosage strengths so that the patient can be administered one dosage unit per day, but the amount of S1P receptor modulator or agonist administered can be titrated upwards until therapy commences at the standard daily dosage. For example, the kit may comprise 2, 3 or 4 e.g. three different dosage forms. In an aspect, the kit may comprise a pack, e.g. a pack containing 1-5 e.g. 2-4 e.g. three different dosage forms. The pack may comprise individual storage portions each portion containing the patient's daily dosage for a given day during the course of treatment. The daily dosage may be made up of one or more of the different dosage forms. In an aspect of this embodiment, the kit comprises a blister pack containing 2-4 e.g. three different dosage forms in which the blisters in the pack contain the daily dosages for administration to the patient during the initial treatment phase, wherein the daily dosage is made up of one or more of the different dosage forms. In an aspect of this embodiment, the pack e.g. the blister pack may comprise a number of blisters corresponding to the number of days of the initial treatment period. In another aspect, the blister pack may also contain one or more blisters containing the final therapeutic dose e.g. so that the total treatment period including the low dosage and therapeutic dosage form lasts for a clinically convenient period of time e.g. one week or two weeks.

In yet another embodiment of the invention, there is provided:

5.1 A method for treating an autoimmune disease in a subject in need thereof, comprising administering to the subject, a daily dosage of compound A or a pharmaceutically acceptable salt thereof, in an amount as herein above defined.

5.2. The method as defined in 5.1, wherein the autoimmune disease is multiple sclerosis.

In yet another embodiment of the invention, there is provided:

6.1 A method for assessing the need or suitability of a patient for a treatment regimen as described above (e.g. in any of the specified aspects or embodiments of the invention), comprising the steps of:
  (i) determining whether the patient to be treated with an S1P receptor modulator or agonist is in a category for which the use of a treatment regimen as described above may be beneficial; and
  (ii) if the patient falls within this category, treating the patient using a treatment regimen as described above.

6.2 The method as defined in 6.1 wherein the patient may be in the above category if he or she suffers from or is susceptible to heart failure, arrhythmias, high grade atrio-ventricular blocks or sick sinus syndrome or has a history of syncopal episodes; or is undergoing beta blocker or anti-arrhythmic treatment, e.g. is under treatment with anti-arrhythmic drugs; or has undergone an interruption or treatment holiday in the maintenance dosage regime e.g. a holiday of greater than 4 days, greater than 6, 8, 10, 12 or 14 days.

The regimen of S1P receptor modulator or agonist which is administered to the subject according to the invention may be given either during or at the beginning of an autoimmune disease therapy, e.g. during the initial 10 days, or after an interruption of S1P receptor modulator or agonist therapy for example an interruption of more than 4 days, for example more than 6, 8 or 10 days, more than 12 days or more than 14 days.

Utility of an S1P receptor modulator or agonist dosage regimen in treating diseases and conditions as hereinabove specified may be demonstrated in standard animal or clinical tests, e.g. in accordance with the methods described hereinafter.

EXAMPLE 1

Increasing doses of Compound A starting at 0.25 mg o.d. and ending at the maximal therapeutic dose of 10 mg o.d. are given to 28 subjects over 12 days as specified in Table 1 below. A placebo group and a positive control group receiving the 10 mg final therapeutic dose are also included in the study (each of 14 subjects).

TABLE 1

| | Day | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| DT#1 (14 subjects) dose (mg) | 0.25 | 0.25 | 0.25 | 0.5 | 1 | 2 | 4 | 8 | 10 | 10 | 10 | 10 |
| DT#2 (14 subjects) dose (mg) | 0.25 | 0.25 | 0.5 | 0.75 | 1.25 | 2 | 3 | 5 | 8 | 10 | 10 | 10 |
| Placebo (14 subjects) | pbo | pbo | pbo | pbo | pbo | pbo | pbo | pbo | pbo | pbo | pbo | pbo |
| 10 mg dose (14 subjects) | 10 | 10 | 10 | 10 | 10 | 10 | 10 | 10 | 10 | 10 | 10 | 10 |

On Day −1 (baseline), subjects undergo baseline assessments including 24 hour holter monitoring and telemetry assessments. Subjects remain on continuous telemetry, starting before breakfast on Day −1 and proceeding throughout the administration period up to Day 13 (24 hour after the last dose). Over this 13 day duration of continuous heart rate collection for each subject, one heart rate value is obtained every minute ('minute unit heart rate'), representing the average heart rate value over that minute. The heart rate database for each subject contains approximately 17,280 data points (13 days×24 hr×60 min).

Pharmacodynamic and safety assessments are performed up to 24 hours post last dose. Heart rhythm is assessed via 24 hr continuous holter monitoring on Day −1, Day 1, Day 11 and Day 12. For each dosing for each subject, the drug is administered as closely as practically possible to the time administered on Day −1. Safety assessments includes physical examinations, vital signs and body measurements, 12-lead ECG evaluations, standard clinical laboratory evaluations hematology, blood chemistry, urinalysis, adverse event and serious adverse event monitoring.

The daily chronotropic effect is defined as the percent decrease in $HR_{min}$ between two consecutive days. It is calculated on days 1 to 12.

24-hour continuous Holter-ECG data are captured via a digital Holter monitor (12-lead, on Days −1, 1, 6, and 8), and transferred for interpretation and reporting. Holter monitoring starts approximately at 7:00 and the time of dose administration is regarded as the time "0 hours". Holter "cuts" are derived from the dataset at 1 hour intervals starting from Day −1 and continuing for 24 hours or the end of the cleaned Holter monitoring dataset.

Cardiac conduction intervals: arrhythmia monitoring includes the frequency and duration of sinus pauses (>2 sec and >3 sec) and atrio-ventricular blocks. Frequency and duration of atrial and ventricular ectopy and sinus rhythm are also recorded. The daily chronotropic effect is defined as the percent decrease in $HR_{min}$, (minimum heart rate) between two consecutive days. It is calculated on days 1 to 12.

Results:

Heart Rate

The variation in daily minimum heart rate, $HR_{min}$ (minimum of 24 hourly mean heart rates) over the course of the study is shown in FIG. 1.

In the placebo group, daily average heart rate varied by approximately 5 BPM (bits per min) over the course of the study with a trend for heart rate to increase approximately 3-4 BPM from Day −1 to Day 2.

The compound A, 10 mg treatment group manifested a significant decrease in heart rate of approximately 8 BPM from Day −1 to Day 1 followed by an increase in heart rate of approximately 5 BPM from Day 1 to Day 2 and a further increase of approximately 3 BPM from day 2 to day 4. Both Compound A titration groups manifest a gradual decrease in heart rate of approximately 1-2 BPM per day to give a total reduction of approximately 4-5 BPM over the first seven days of the dose titration, following which, the heart rate increased to approximately the placebo level over the next 2-3 days.

The initiation of the 10 mg dose of compound A on Days 8 and 9 of the study did not result in a significant dip in heart rate compared to the heart rate measured in the preceding days.

These results indicate that the use of a dose titration regimen according to the invention attenuates the negative chronotropic effect seen on Day 1 of compound A 10 mg dose treatment initiation.

Additional Benefits

Table 2 below shows the number of ventricular and supraventricular ectopies (VEs and SVEs respectively) and the total number of pauses greater than 2 seconds observed during the trial for patients on all four arms of the study.

TABLE 2

|  | Category | DT#1 (N = 14) n (%) | DT#2 (N = 14) n (%) | 10 mg (N = 14) n (%) | PBO (N = 14) n (%) |
| --- | --- | --- | --- | --- | --- |
| Total number* of SVEs | 0-10 | 1 (7.1%) | 0 | 1 (7.1%) | 1 (7.1%) |
|  | 11-20 | 3 (21.4%) | 1 (7.1%) | 2 (14.3%) | 3 (21.4%) |
|  | 21-50 | 2 (14.3%) | 4 (28.6%) | 5 (35.7%) | 4 (28.6%) |
|  | >50 | 8 (57.1%) | 9 (64.3%) | 6 (42.9%) | 6 (42.9%) |
| Total number* of VEs | 0-5 | 3 (21.4%) | 3 (21.4%) | 6 (42.9%) | 6 (42.9%) |
|  | 6-10 | 5 (35.7%) | 2 (14.3%) | 4 (28.6%) | 2 (14.3%) |
|  | 11-30 | 4 (28.6%) | 5 (35.7%) | 1 (7.1%) | 5 (35.7%) |
|  | >30 | 2 (14.3%) | 4 (28.6%) | 3 (21.4%) | 1 (7.1%) |
| Total number* of pauses >2 secs | 0 | 10 (71.4%) | 13 (92.9%) | 10 (71.4%) | 14 (100.0%) |
|  | 1 | 1 (7.1%) | 0 | 1 (7.1%) | 0 |
|  | >1 | 3 (21.4%) | 1 (7.1%) | 3 (21.4%) | 0 |

*At any time during the 12-day treatment period.

This table shows that the second titration regimen DT#2 (in which the dosage is increased in a Fibonacci sequence) gives a lower number of heart pauses greater than 2 seconds than the other active treatment regimens.

The invention claimed is:

1. A method of administering to a subject in need thereof a medication comprising a S1P receptor agonist, whereby said S1P receptor modulator or agonist is given at a dosage lower than the standard daily dosage of said S1P receptor modulator or agonist during the initial period of treatment and then the dosage is increased, up to the standard daily dosage of said S1P receptor agonist.

2. The method according to claim 1, wherein the medication is for the treatment of an autoimmune condition.

3. The method according to claim 2 wherein the autoimmune condition is multiple sclerosis.

4. The method according to claims 1, wherein the S1P receptor agonist is a compound of formula Ia or Ib

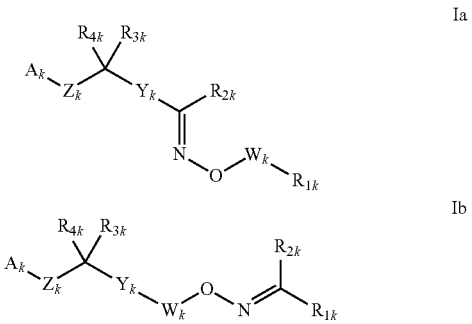

wherein
$A_k$ is —$COOR_{5k}$, —$OPO(OR_{5k})_2$, —$PO(OR_{5k})_2$, —$SO_2OR_{5k}$, —$POR_{5k}OR_{5k}$ or 1H-tetrazol-5-yl, $R_{5k}$ being H or $C_{1-6}$alkyl;
$W_k$ is a bond, $C_{1-3}$alkylene or $C_{2-3}$alkenylene;
$Y_k$ is $C_{6-10}$aryl or $C_{3-9}$heteroaryl, optionally substituted by 1 to 3 radicals selected from halogen, OH, $NO_2$, $C_{1-6}$alkoxy; halo-substituted $C_{1-6}$alkyl and halo-substituted $C_{1-6}$alkoxy;
$Z_k$ is chosen from

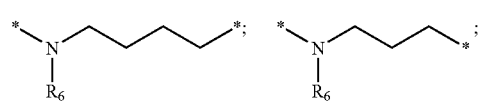

-continued

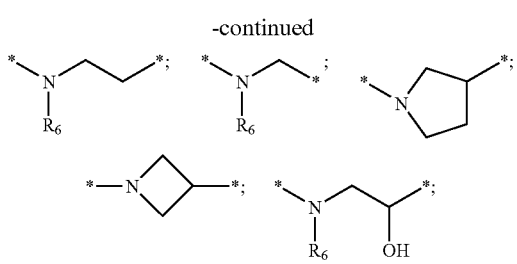

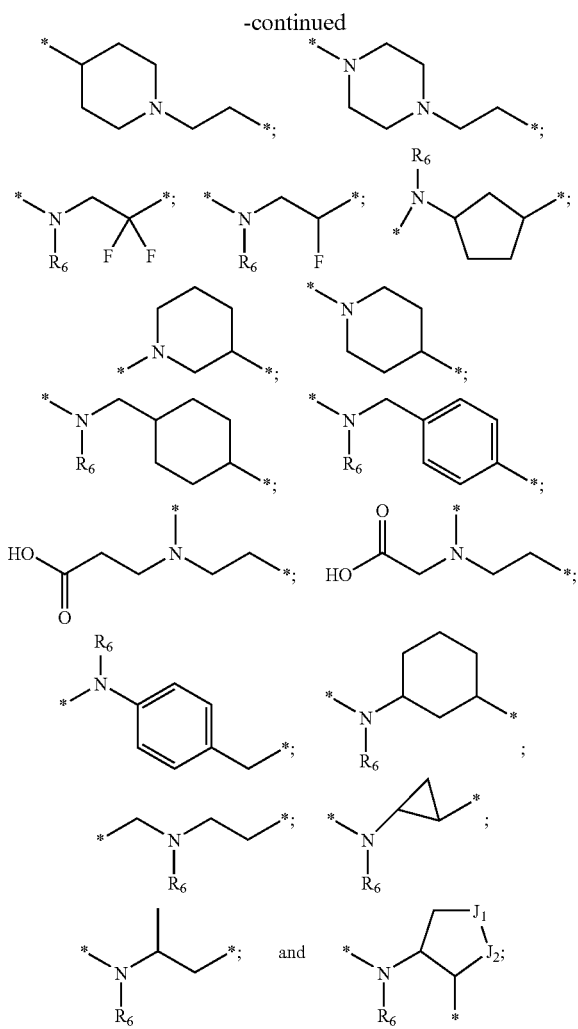

wherein the asterisks of $Z_k$ indicate the point of attachment between —$C(R_{3k})(R_{4k})$—and $A_k$ of Formula Ia or Ib, respectively; $R_6$ is chosen from hydrogen and $C_{1-6}$alkyl; and $J_1$ and $J_2$ are independently methylene or a heteroatom chosen from S, O and $NR_{5k}$; wherein $R_{5k}$ is chosen from hydrogen and $C_{1-6}$alkyl; and any alkylene of $Z_k$ can be further substituted by one to three radicals chosen from halo, hydroxy, $C_{1-6}$alkyl; or $R_6$ can be attached to a carbon atom of $Y_k$ to form a 5-7 member ring;

$R_{1k}$ is $C_{6-10}$aryl or $C_{3-9}$heteroaryl, optionally substituted by $C_{1-6}$alkyl, $C_{6-10}$aryl, $C_{6-10}$aryl$C_{1-4}$alkyl, $C_{3-9}$heteroaryl, $C_{3-9}$heteroaryl$C_{1-4}$alkyl, $C_{3-8}$cycloalkyl, $C_{3-8}$cycloalkyl$C_{1-4}$alkyl, $C_{3-8}$heterocycloalkyl or $C_{3-8}$heterocycloalkyl$C_{1-4}$alkyl; wherein any aryl, heteroaryl, cycloalkyl or heterocycloalkyl of $R_{1k}$ may be substituted by 1 to 5 groups selected from halogen, $C_{1-6}$alkyl, $C_{1-6}$ alkoxy and halo substituted-$C_{1-6}$alkyl or —$C_{1-6}$alkoxy;

$R_{2k}$ is H, $C_{1-6}$alkyl, halo substituted $C_{1-6}$alkyl, $C_{2-6}$alkenyl or $C_{2-6}$alkynyl: $R_{2k}$ is in particular methyl; and each of $R_{3k}$ or $R_{4k}$, independently, is H, halogen, OH, $C_{1-6}$alkyl, $C_{1-6}$alkoxy or halo substituted $C_{1-6}$ alkyl or $C_{1-6}$alkoxy;

and the N-oxide derivatives thereof or prodrugs thereof, or a pharmacologically acceptable salt, solvate or hydrate thereof.

5. The method according to claim 4, wherein the S1P receptor agonist is Compound A or a pharmaceutically acceptable salt thereof.

6. The method according to claim 1, wherein a sub-therapeutic dose of the S1P receptor agonist that is 80 fold less, 40 fold less, 10-fold less or 4-fold less than the standard daily dosage is administered during the initial period of treatment.

7. The method according to claim 1 wherein, during the initial period of treatment, the administered dosage is increased stepwise.

8. The method according to claim 7, wherein the administered dosage is increased stepwise such that the dosage administered on a specific day during the initial period of treatment is the sum of the dosages administered on the previous two days within a range of ±40%.

9. A method for treating a subject in need thereof comprising administering a S1P receptor agonist which induces a negative chronotropic effect in heart rate, to the subject at a daily dosage which is lower than the standard daily therapeutic dosage during an initial period of treatment and thereafter commencing the administration of said S1P receptor modulator or agonist at the required standard daily therapeutic dosage.

10. The method of claim 9, wherein the patient is suffering from an autoimmune condition.

11. The method of claim 10 wherein the autoimmune condition is multiple sclerosis.

12. The method of 9, wherein the S1P receptor agonist is Compound A or a pharmaceutically acceptable salt thereof or prodrug thereof.

13. A method of ameliorating or preventing a negative chronotropic side effect associated with a treatment using an S1P agonist of a subject suffering from an autoimmune disease, comprising administering to the subject in need thereof, said S1P receptor agonist at a daily dosage which is lower than the standard daily dosage during an initial treatment period and raising the daily dosage stepwise up to the standard daily dosage.

14. The method of 13, wherein the S1P receptor agonist is Compound A or a pharmaceutically acceptable salt thereof or prodrug thereof.

15. The method according to claim 9, comprising administering to the subject, a S1P receptor agonist at a daily dosage which is lower than the standard daily dosage during the first 10 days and raising the daily dosage stepwise up to the standard daily dosage.

16. The method according to claim 13, comprising administering to the subject, a S1P receptor agonist at a daily dosage which is lower than the standard daily dosage during the first 10 days and raising the daily dosage stepwise up to the standard daily dosage.

* * * * *

UNITED STATES PATENT AND TRADEMARK OFFICE
CERTIFICATE OF CORRECTION

PATENT NO. : 8,492,441 B2
APPLICATION NO. : 12/655049
DATED : July 23, 2013
INVENTOR(S) : Eric Legangneux It is certified that error appears in the above-identified patent and that said Letters Patent is hereby corrected as shown below:

In the Claims

Claim 1, Column 19, Line 63, "S1P receptor modulator or agonist" should read --S1P receptor agonist--.

Claim 1, Column 19, Lines 64-65, "S1P receptor modulator or agonist" should read --S1P receptor agonist--.

Claim 9, Column 22, Lines 28-29, "S1P receptor modulator or agonist" should read --S1P receptor agonist--.

Claim 13, Column 22, Lines 39-40, "an S1P agonist" should read --a S1P receptor agonist--.

Signed and Sealed this
First Day of November, 2022

Katherine Kelly Vidal
Director of the United States Patent and Trademark Office